US008377870B2

(12) United States Patent
Takeuchi et al.

(10) Patent No.: US 8,377,870 B2
(45) Date of Patent: Feb. 19, 2013

(54) ANTIMICROBIAL AQUEOUS SOLUTION AND ITS PREPARATION METHOD

(75) Inventors: Setsuo Takeuchi, Tokyo (JP); Yasushi Yoshikawa, Tokyo (JP)

(73) Assignee: Dentrochemical Co., Ltd., Tokyo (JP), part interest ( * ) Notice: Subject to any disclaimer, the term of this patent is extended or adjusted under 35 U.S.C. 154(b) by 315 days.

(21) Appl. No.: 12/738,021

(22) PCT Filed: Oct. 19, 2009

(86) PCT No.: PCT/JP2009/005432
§ 371 (c)(1),
(2), (4) Date: Apr. 14, 2010

(87) PCT Pub. No.: WO2010/052836
PCT Pub. Date: May 14, 2010

(65) Prior Publication Data
US 2012/0015869 A1    Jan. 19, 2012

(30) Foreign Application Priority Data

Nov. 6, 2008  (JP) ................................. 2008-285655

(51) Int. Cl.
*A01N 37/18*    (2006.01)
*A61K 38/00*    (2006.01)
*A61P 31/00*    (2006.01)
*A61P 31/04*    (2006.01)

(52) U.S. Cl. ......................................... 514/2.3; 514/2.4
(58) Field of Classification Search ................... 514/2.3, 514/2.4
See application file for complete search history.

(56) References Cited

FOREIGN PATENT DOCUMENTS

| JP | 05-219925 | * | 8/1993 |
| JP | 07-135943 | | 5/1995 |
| JP | 2000-270821 | | 10/2000 |

OTHER PUBLICATIONS

Kabara et al. Antimicrobials in Food. CH. 11, Medium-Chain Fatty Acids and Esters. 2005, 327-360.*
Compass Foods, The GRAS status of sucrose monoesters of lauric acid, palmitic acid and stearic acid as emulsifyiing agents for flavors used in fruit flavored beverages, p. 1-126, Aug. 29, 2008.*
Machine English Translation of JP 05-219925, Aug. 1993.*
S. Takeuchi et al. A Preservation System Combining Parabens and Polylysine, Bokin Bobai, Vol. 31, No. 12, pp. 706-710, 2003, abstract only.
H. Nikaido et al. Molecular Basis of Bacterial Outer Membrane Permeability, Microbiological Review, pp. 1-32, Mar. 1985.

* cited by examiner

*Primary Examiner* — Ileana Popa
*Assistant Examiner* — Genevieve S Alley
(74) *Attorney, Agent, or Firm* — Howson & Howson LLP

(57) ABSTRACT

The antimicrobial aqueous solution of the present invention comprises an original undiluted aqueous solution containing: 25 μg/ml to 50 μg/ml of an amphipathic preservative comprising a monoglycerol monolaurate; and 12.5 μg/ml to 30 μg/ml of an ε-polylysine. In preparing the antimicrobial aqueous solution, dissolution of the amphipathic antimicrobial can be promoted by addition of a sucrose monolaurate and by heating to 35° C. to 60° C. This antimicrobial aqueous solution can be used effectively, even within a range of concentrations lower than concentrations to be typically used for amphipathic antimicrobials. It is possible to adopt a diglycerol monolaurate, instead of the monoglycerol monolaurate.

18 Claims, 2 Drawing Sheets

ANTIMICROBIAL AQUEOUS SOLUTION AND ITS PREPARATION METHOD

BACKGROUND OF THE INVENTION

1. Field of the Invention

The present invention relates to: an antimicrobial aqueous solution containing an ε-polylysine and an amphipathic antimicrobial as constituent components in amounts of microgram units relative to 1 ml of water, and its preparation method; and more particularly to an antimicrobial aqueous solution which adopts, as the amphipathic antimicrobial, monoglycerol monolaurate (which may also be called "monolaurin") or diglycerol monolaurate in a manner to use it combiningly with an ε-polylysine and to add a sucrose monolaurate as a solubilizer into the solution, and its preparation method.

2. Description of the Related Art

Higher organisms including human species live in a manner daily exposed to a wide variety of and an extremely large number of micro-organisms, from birth to death. Such micro-organisms include good bacteria and bad bacteria, so that microfloras (habitat distribution of micro-organisms) of the higher organisms have been fluctuated within certain ranges due to influences of the environment. Further, the human species have been drastically changed in lifestyle at recent times, and the influence of the environmental changes such as due to industrial activities is coming up to the area of micro-organisms. After the latter half of the 20th century, numerous antibiotics have been found out, thereby enabling to counteract serious diseases due to pathogenic microbes. To the contrary, such antibiotics tend to be overused because they allow for counteractions to serious diseases with ease, to resultingly bring about generation of antibiotics resistant microbes, which is to be counteracted as soon as possible. Moreover, there is a problem of a group of bacteria called gram negative bacteria which are originally nonsensitive to lipophilic antibiotics. These bacteria are characterized in that, whereas gram positive bacteria each have a cell surface comprising two layers of a cytoplasmic membrane and a cell wall, the gram negative bacteria each additionally include a strong membrane called an outer membrane as an outermost layer, which outer membrane acts as a barrier against lipophilic antibiotics tending to invade the gram negative bacteria from the outside thereof. Effective substances capable of invading such gram negative bacteria, are less in amount of existence. It is said that advanced persons, who have been frequently subjected to opportunities of usage of antibiotics for many years, have internal microfloras including predominant gram negative bacteria. As an example, pathogenic bacteria of geriatric pneumonia are frequently *Pseudomonas* being in gram negative nature and having a strong resistance against lipophilic antibiotics, so that the medical scenes undergo difficulty in medical treatments therefor (see Non-Patent Document 1, for example).

Upon occurrence of an epidemic disease under such circumstances, passive measures are taken, such as local dispersion of an antiseptic solution, and sterilization of hands of medical professionals and workers. Unfortunately, active techniques have not been found to previously eliminate possibilities of epidemic diseases, even at present where scientific techniques have been so advanced. One of the reasons thereof is that most of antiseptic solutions also have toxicities to humans as well as residual properties, so that such antiseptic solutions are not allowed to be prophylactically dispersed. Then, attention is to be directed to a presence of those among preservatives to be used for foods and the like, which are relatively low in toxicity. However, they are generally mild in antimicrobial activity and have antimicrobial spectra different from one another. As such, expectation has been redirected to a complementary or synergistic combined system, based on a combination of multiple preservatives. Specifically, it has been disclosed that food preservatives each provided by adding a protamine to a glycerol monomiddle length fatty acid ester and an ε-polylysine, are made to have broad antimicrobial spectra against various micro-organisms (see Patent Document 1, for example). Further, food preservatives have been disclosed each containing, as active ingredients: an aliphatic monoglycerin ester of a fatty acid having 8 to 12 carbon atoms; and an ε-polylysine; (see Patent Document 2, for example). Moreover, preservatives have been disclosed each having a polylysine, and a glycerin monolaurate, i.e., monolaurin (see Patent Document 3, for example).

However, these problems including the above-mentioned problem of antibiotics resistant microbes have not been solved yet. Then, the antibacterial agents disclosed in the Patent Documents 1 to 3 have been investigated to reveal that the ε-polylysine and the monoglycerol monolaurate have antimicrobial activities which are exhibited under the requirement that these components are combined with each other and used together with protamine or glycine so as to enhance the antimicrobial effects of the combined substances. Further, although the antimicrobial effects have been obtained by using these components at higher concentrations, respectively, sufficient effects against gram negative bacteria have not been obtained yet in any of the Patent Documents.

Further, monolaurin has been restricted in usage, because of its drawbacks that monolaurin is particularly inactive against gram negative bacteria and exhibits a low water solubility. In turn, although an ε-polylysine has been and is being noticed as a rare one of substances which are active even against *Pseudomonas* as gram negative bacteria, it is impossible to confirm an antimicrobial reinforce effect for an amphipathic antimicrobial insofar as at a usage concentration at which the antimicrobial action of ε-polylysine is expected. This is because, cell surfaces of micro-organisms are minus charged and the ε-polylysine is plus charged, so that the ε-polylysine is attached in an extremely large amount onto surfaces of the micro-organisms. Thus, it appears that usage of ε-polylysine at a high concentration causes the bonded long molecules of ε-polylysine to cover cell surfaces of micro-organisms, so that the permeability of monolaurin through cytoplasmic membranes is obstructed and the antimicrobial activity of the monolaurin is not exhibited.

Meanwhile, since an agar impression material is provided for directly collecting a mouth impression of a patient by a hand of a dentist, strict safety is demanded legally. However, none of the preservatives usable therefor has possessed a satisfactory antimicrobial effect. Then, the present inventors have noticed a combination of an ε-polylysine with an amphipathic antimicrobial and investigated addition amounts thereof, to resultingly find out that an antimicrobial activity can be reinforced by combining an ε-polylysine with an amphipathic antimicrobial at lower concentrations of microgram units relative to 1 ml of water, respectively. The present inventors have also noticed a point that the slight water soluble monolaurin is suspended in water, and have searched for a solubilization agent of monolaurin into water (hereinafter, the solubilization agent is called "solubilizer"), thereby resultingly finding out that the monolaurin dissolves, in an amount several times its solubility in water, in such a water containing a sucrose monolaurate added therein, to attain a transparent aqueous solution to thereby further progress the antimicrobial activity. In this respect, it has been found out that, when the monolaurin is provided not in a state of suspension but in a state of complete aqueous solution, there can be obtained such a collaborated effect that the monolaurin sufficiently permeates through cell surfaces of gram negative bacteria even under the influence of ε-polylysine, to exhibit an effectiveness of the monolaurin as an antibacterial agent having a broad spectrum and to further expand the spectrum up to gram negative bacteria.

It also has been found out that the addition of sucrose monolaurate exhibits not only the solubilizing effect but also such an effect that precipitated monolaurin is not caused even after a long-term storage. It has been further found out that the same effect as monolaurin can be exhibited, even when adopting a diglycerol monolaurate at a lower concentration to be handled at microgram units relative to 1 ml of water. The present invention has been narrowly completed, based on these knowledges.

[Patent Document 1] JP7-135943A1 (Claims, paragraph [0002], and paragraph [0004])

[Patent Document 2] JP2000-270821A1 (claims 1 and 2)

[Patent Document 3] JP11-228308A1 (claims 1 and 2)

[Non-Patent Document] H. NIKAIDO and M. VAARA, Microbiological Reviews, March 1985, p 1-32

SUMMARY OF THE INVENTION

It is therefore an object of the present invention to provide: an antimicrobial aqueous solution which is safe and which exhibits a broad antimicrobial effect, particularly an excellent antimicrobial effect against gram negative bacteria, by usage of an ε-polylysine and an amphipathic antimicrobial even at concentrations lower than typically used concentrations, respectively; and its preparation method.

The object of the present invention is achieved by the following inventions.

(1) The present invention resides in an antimicrobial aqueous solution comprising:

an aqueous solution containing:

25 μg/ml to 50 μg/ml of an amphipathic antimicrobial comprising a monoglycerol monolaurate;

12.5 μg/ml to 30 μg/ml of an ε-polylysine; and 0.1 μg/ml to 100 μg/ml of a sucrose monolaurate.

(2) Further, the present invention resides in an antimicrobial aqueous solution comprising:

an aqueous solution containing:

3.25 μg/ml to 50 μg/ml of an amphipathic antimicrobial comprising a diglycerol monolaurate;

8 μg/ml to 30 μg/ml of an ε-polylysine; and 0.1 μg/ml to 100 μg/ml of a sucrose monolaurate.

(3) The present invention resides in a preparation method of an antimicrobial aqueous solution, comprising the steps of:

adding and dissolving an amphipathic antimicrobial comprising a monoglycerol monolaurate at a ratio of 25 μg to 50 μg relative to 1 ml of water, into a water containing a sucrose monolaurate at a ratio of 0.1 μg to 100 μg relative to 1 ml of water; and adding and dissolving an ε-polylysine at a ratio of 12.5 μg to 30 μg relative to 1 ml of water, into the obtained aqueous solution of the amphipathic antimicrobial.

(4) In the preparation method (3) of an antimicrobial aqueous solution, it is preferable that, when the monoglycerol monolaurate is dissolved into the water containing the sucrose monolaurate, the dissolution is conducted by heating up to 35° C. to 60° C.

(5) The present invention resides in a preparation method of an antimicrobial aqueous solution, comprising the steps of:

adding and dissolving an amphipathic antimicrobial comprising a diglycerol monolaurate at a ratio of 3.25 μg to 50 μg relative to 1 ml of water, into a water containing a sucrose monolaurate at a ratio of 0.1 μg to 100 μg relative to 1 ml of water; and adding and dissolving an ε-polylysine at a ratio of 8 μg to 30 μg relative to 1 ml of water, into the obtained aqueous solution of the amphipathic antimicrobial.

(6) In the preparation method (5) of an antimicrobial aqueous solution, it is preferable that, when the diglycerol monolaurate is dissolved into the water containing the sucrose monolaurate, the dissolution is conducted at a temperature in a range from an ordinary temperature to a room temperature.

It is within a technical scope of the present invention to adopt an alcohol-containing aqueous solution typically used in this technical field, as the aqueous solution to be used in the present invention. The ε-polylysine (ε-polylysine, S. Shima et. al., J. Antibiotics, 37: p 1455-1459, 1984) to be used in the present invention is known, and may be obtained by any methods including a method to exemplarily culture *Streptomyces albulus* ssp. *lysinopolymerus* which is an ε-polylysine producing strain, to isolate an ε-polylysine from the obtained culture, and to purify it (JP59-20359B2). The ε-polylysine is a substance which has an acute toxicity, has an LD50>10.0 g/kg, is negative in a mutagenicity test, exhibits a strong antimicrobial activity against gram positive bacteria and gram negative bacteria, exhibits a relatively weak activity against true fungi, has a wider active pH range, is stable against heating, and is water soluble. ε-polylysines are listed in an existing food product additive list (Health, Labor and Welfare Ministry), and are widely used as stable preservatives in food preservatives and the like. ε-polylysines are basic homopeptide mixtures with peptide-bonded 20-30 residues of L-lysine as an essential amino acid.

Two different binding forms of lysines are found for polylysines, and an ε-polylysine is a peptide including lysines where those amino groups at ε sites (fifth sites) of lysines, which amino groups are each located at the end of each applicable lysine, are continuously amide-bonded to one another, lysine by lysine. In turn, an α-polylysine as an isomer is a peptide where amino groups at α-site (first site) of lysines are continuously amide-bonded to one another, lysine by lysine. Comparing chemical structures of both, the ε-polylysine is a molecule which is straightly long, smooth, and flexible, whereas the α-polylysine is a massive and stiff molecule. The molecule of ε-polylysine is a polycationic peptide being at least 30 nanometers in length and having the same number of amino radicals as that of mutually bonded lysine residues. When the plus charged ε-polylysine is electrostatically and firmly bound to minus charged hydrophilic cell surfaces of micro-organisms, physical stresses are applied to the cell surfaces, and simultaneously therewith, the electric charges are neutralized, so that the cell surfaces are turned to be a lipophilic tendency. As a result, it is supposed that affinities are increased between the amphipathic antimicrobial having a combined hydrophobic portion and the cell surfaces, thereby bringing about an increased antimicrobial activity.

Although an ε-polylysine is a rare one of substances which are active even against *Pseudomonas*, it is impossible to confirm an antimicrobial reinforce effect for an amphipathic antimicrobial insofar as at a usage concentration, i.e., at a concentration of the ε-polylysine exceeding 30 μg/ml at which only the antimicrobial action of ε-polylysine is expected, because cell surfaces of micro-organisms are then covered by the ε-polylysine so that the permeability of the amphipathic antimicrobial through cell surfaces is obstructed. The lower limit of addition amount of ε-polylysine is 12.5 µg/ml in case for monolaurin, and 3.25 µg/ml in case for dilaurin. Addition amounts of ε-polylysine less than the above-described lower limits fail to sufficiently exhibit effects collaborated with amphipathic antimicrobials.

The term "amphipathic antimicrobial" used in the present invention refers to a preservative having both a lipophilic portion and a hydrophilic portion. Monolaurin (monolauryl glycerol, A. J. Conley and J. J. Kabara, Antimicrobial Agents and Chemotherapy, 4: p 501-506 (1973)) is one kind of the amphipathic antimicrobials. This monolaurin may be obtained by any method. The monolaurin, where one molecule of lauric acid is ester-bonded to only one of three hydroxyl groups of one molecule of glycerol, is desirable. Particularly, the monolaurin, which is a glycerol monoester of a saturated fatty acid having a 12-carbon chain, is outstandingly strong in antimicrobial activity among the same types of glycerol mono-fatty acid esters. While the reason thereof is said to be deeply related to an affinity of the monolaurin with cytoplasmic membranes of procaryotic micro-organisms (bacteria), details of the mechanism of the antimicrobial activity have not been clarified yet.

As an amphipathic antimicrobial other than the above, diglycerol monolaurate is used. The diglycerol monolaurate is excellent in water solubility. While monoglycerol monolaurate is usable within a range of 25 µg/ml to 50 µg/ml, diglycerol monolaurate is usable within a range of 3.25 µg/ml to 50 µg/ml. Addition amounts of the amphipathic antimicrobial less than the above-described lower limits fail to exhibit effects collaborated with the ε-polylysine. Further, addition amounts of the amphipathic antimicrobial exceeding 50 µg/ml not only fail to exhibit a synergistic effect with the ε-polylysine, but also rather obstruct such an effect. Moreover, although diglycerol monolaurate is excellent in water solubility among amphipathic substances so that a desired water solubility is obtainable by the diglycerol monolaurate without addition of a sucrose monolaurate, the diglycerol monolaurate can be dissolved more rapidly by the addition of the sucrose monolaurate.

The ε-polylysine as one constituent component of the antimicrobial aqueous solution of the present invention has a first feature that the ε-polylysine is electrostatically bonded to cell surfaces of micro-organisms to thereby modify functions of the cell surfaces even at a lower concentration where the antimicrobial action (bacteriostatic action) possessed by the ε-polylysine itself is not expected, thereby exhibiting a physiological action to remarkably enhance a permeability of the monolaurin or diglycerol monolaurate as the combined antimicrobial component. The ε-polylysine has a second feature that, when the monolaurin or diglycerol monolaurate having a higher antimicrobial action is selected as the amphipathic antimicrobial of the combined components and as a main constituent component, the amphipathic antimicrobial is allowed to act, by virtue of the collaborated effect of the ε-polylysine, on micro-organisms even at a low concentration of µg/ml units of the amphipathic antimicrobial at which concentration the amphipathic antimicrobial has been inactive insofar as by usage by itself, so that the amphipathic antimicrobial is caused to exhibit a remarkable antimicrobial effect. The antimicrobial aqueous solution of the present invention is usable by diluting it with a deionized water upon usage within a range where the antimicrobial activity effect is obtainable depending on a purpose of use, and specifically, 2-fold to 16-fold. The method to dilute the antimicrobial aqueous solution of the present invention is not particularly limited. However, when the ε-polylysine is to be fixed in amount and to be contained in a constant amount in consideration of a ratio between the amount of ε-polylysine and the amount of amphipathic antimicrobial, it is preferable to dilute an aqueous solution containing the amphipathic antimicrobial added therein, in a manner of 2-fold, 4-fold, 8-fold, or 16-fold, with an aqueous solution containing the constant amount of ε-polylysine dissolved therein. The content of the ε-polylysine in the solution diluted by such a diluting method, is kept constant.

It is naturally required to select a concentration of a formulated solution so that the content of the amphipathic antimicrobial is not decreased down to an amount less than the lower limit (25 µg/ml in case of monolaurin, and 3.25 µg/ml in case of dilaurin) with dilution.

It is preferable that the antimicrobial aqueous solution of the present invention is used, without adding thereinto any other additives such as other preservatives, surfactants (except for polyalcohol monolaurate), antioxidants, ultraviolet absorbers, fragrant materials, pigments, and the like, as well as without adjustment of pH. Namely, the aqueous solution is to be used within a range of pH 4.0 to 8.0, in a state that the components to be used in the present invention have been dissolved therein.

Further, the sucrose monolaurate is used in an amount to an extent required to cause the components of the antimicrobial aqueous solution to dissolve in each other, and this amount is also made adjustable depending on the amounts of the components of the antimicrobial aqueous solution. Preferably, the sucrose monolaurate is used in an addition amount within a range of 0.1 µg/ml to 100 µg/ml, and more preferably 0.1 µg/ml to 50 µg/ml.

Particularly, the amount of the sucrose monolaurate to be added for the diglycerol monolaurate may be smaller than the addition amount than that for the monolaurin, i.e., may be 0.1 µg/ml to 50 µg/ml, preferably 0.1 µg/ml to 30 µg/ml. Addition amounts of the sucrose monolaurate less than 0.1 µg/ml fail to sufficiently exhibit an effect thereof as a solubilizer. Further, exceeding 100 µg/ml does not result in a remarkable difference of a promoting effect, so that the addition amount is limited to within the above-mentioned range.

To prepare an antimicrobial aqueous solution in a small volume by using the ε-polylysine and monolaurin, it is possible to use an aqueous ethanol solution of 30-60%. Other additives should not be added without careful consideration, because the activity is influenced thereby. The monolaurin to be combined with the dilute ε-polylysine may be obtained by any method, insofar as with a high purity of 95% or more.

Examples of the preparation method of the antimicrobial aqueous solution of the present invention include the following configurations:

(a) A method characterizedly configured to: dissolve 25 µg/ml to 50 µg/ml of an amphipathic antimicrobial comprising a monoglycerol monolaurate into 1 ml of water; and add 12.5 µg/ml to 30 µg/ml of an ε-polylysine into the obtained aqueous solution of the amphipathic antimicrobial; wherein the water to be used is preferably a sterilized deionized water, without particularly limited thereto, insofar as adopting a water which does not affect on the ε-polylysine and amphipathic antimicrobial.

In dissolving the respective components into the water, the sucrose monolaurate is firstly added into the water, then the monoglycerol monolaurate is added into the obtained aqueous solution of the sucrose monolaurate, followed by sufficient stirring for dissolution, and the ε-polylysine is added thereto and dissolved therein.

The sucrose monolaurate is used preferably in an addition amount within a range of 0.1 µg/ml to 100 µg/ml, and more preferably 0.1 µg/ml to 50 µg/ml, as noted above.

(b) A method characterizedly configured to: when the monoglycerol monolaurate is dissolved into a water, add the sucrose monolaurate as the solubilizer into the water, and heat the resultant aqueous solution to 35° C. to 60° C. Namely, the sucrose monolaurate as the solubilizer is firstly added into the water, the resultant aqueous solution is heated to 35° C. to 60° C., and then the monoglycerol monolaurate is added into the aqueous solution, followed by stirring for dissolution, to obtain the antimicrobial aqueous solution. At this time, it is also possible that the monoglycerol monolaurate is firstly added into the water, and then the sucrose monolaurate as the solubilizer is added into the resultant aqueous solution, followed by heating thereof up to 35° C. to 60° C., so that the order of the additions is not particularly limited. The heating temperature is preferably 40° C. to 50° C. Heated temperatures below 35° C. not only lead to difficulty in dissolution but also disadvantageously require a longer time for dissolution. Further, heated temperatures higher than 60° C. disadvantageously bring about adverse effects on the added components.

Other configurations of the preparation method of the antimicrobial aqueous solution of the present invention will be described hereinafter:

(c) A method characterizedly configured to: adopt 3.25 μg/ml to 50 μg/ml of a diglycerol monolaurate as an amphipathic antimicrobial; and upon dissolution thereof into a water, dissolve the diglycerol monolaurate into the water while adding a sucrose monolaurate thereinto as a solubilizer.

Although the diglycerol monolaurate is excellent in solubility in water, it is particularly preferable to dissolve the diglycerol monolaurate in water together with addition of a sucrose monolaurate in case of handling at a place subjected to a lower atmospheric temperature, and the addition of the sucrose monolaurate eliminates a possibility of occurrence of precipitation of the diglycerol monolaurate during storage.

The amount of the sucrose monolaurate to be added for the diglycerol monolaurate may be smaller than the addition amount for the monolaurin, i.e., may be 0.1 μg/ml to 50 μg/ml, preferably 0.1 μg/ml to 30 μg/ml.

(d) A method characterizedly configured to: when the diglycerol monolaurate is dissolved into a water in the method (c), the dissolution is conducted at a temperature in a range from an ordinary temperature to a room temperature. Namely, the diglycerol monolaurate is added into the water containing the sucrose monolaurate added therein, and dissolved in the water at a temperature in a range from an ordinary temperature to a room temperature, and then the ε-polylysine is added thereto, followed by stirring for dissolution. The room temperature means about 18° C. and the ordinary temperature means about 25° C., so that the temperature in a range from an ordinary temperature to a room temperature typically means 18° C. to 25° C.

The antimicrobial aqueous solution of the present invention comprises an aqueous solution containing 25 μg/ml to 50 μg/ml of the amphipathic antimicrobial comprising a monoglycerol monolaurate, 12.5 μg/ml to 30 μg/ml of the ε-polylysine, and 0.1 μg/ml to 100 μg/ml of the sucrose monolaurate, thereby exhibiting such excellent effects that the micro-organism modifying action to be exhibited by the ε-polylysine at a lower concentration thereof and the antimicrobial action of the monolaurin are synergetically reinforced, that both the ε-polylysine and monolaurin are biodegradable and are thus free of biological accumulation, and that both of them are adapted to provide a colorless, odorless, tasteless, stable, and safe aqueous solution. Particularly, the antimicrobial aqueous solution has a strong growth restricting action against gram negative bacteria, and thus has an extremely wide application as an antibacterial agent having a broad spectrum.

Note that the antimicrobial aqueous solution of the present invention is usable as a dilute aqueous solution, thereby also exhibiting an effect to be usable at a relatively low cost.

Further, the antimicrobial aqueous solution of the present invention comprises an aqueous solution containing 3.25 μg/ml to 50 μg/ml of the amphipathic antimicrobial comprising a diglycerol monolaurate, 8 μg/ml to 30 μg/ml of the ε-polylysine, and 0.1 μg/ml to 100 μg/ml of the sucrose monolaurate, thereby exhibiting such excellent effects that the micro-organism modifying action to be exhibited by the ε-polylysine at a lower concentration thereof and the antimicrobial action of the diglycerol monolaurate are synergetically reinforced, that both the ε-polylysine and diglycerol monolaurate are biodegradable and are thus free of biological accumulation, and that both of them are adapted to provide a colorless, odorless, tasteless, stable, and safe aqueous solution. Particularly, the antimicrobial aqueous solution has a strong growth restricting action against gram negative bacteria, and thus has an extremely wide application as an antibacterial agent having a broad spectrum.

Note that the antimicrobial aqueous solution of the present invention is usable as a dilute aqueous solution, thereby also exhibiting an effect to be usable at a relatively low cost.

The preparation method of an antimicrobial aqueous solution of the present invention comprises the steps of: adding and dissolving an amphipathic preservative comprising a monoglycerol monolaurate at a ratio of 25 μg to 50 μg relative to 1 ml of water, into an aqueous solution containing a sucrose monolaurate at a ratio of 0.1 μg to 100 μg relative to 1 ml of water; and adding and dissolving an ε-polylysine at a ratio of 12.5 μg to 30 μg relative to 1 ml of water, into the obtained aqueous solution of the amphipathic preservative; thereby exhibiting such an effect that the solubility of the monoglycerol monolaurate in water is increased to promote the permeability of the monoglycerol monolaurate through cell surfaces of bacteria even under the influence of the ε-polylysine, to exhibit an excellent antimicrobial effect against gram negative bacteria by virtue of the synergistic action of both the monoglycerol monolaurate and ε-polylysine.

In the above preparation method of an antimicrobial aqueous solution, when the monoglycerol monolaurate is dissolved into the water containing the sucrose monolaurate, the dissolution is conducted by heating up to 35° C. to 60° C., thereby exhibiting such an effect to further promote dissolution of the monoglycerol monolaurate, which is less soluble, to allow for establishment of a complete aqueous solution of the monoglycerol monolaurate, thereby enabling to progress the antimicrobial effect collaborated with the ε-polylysine even at a lower concentration to be handled in microgram unit.

The preparation method of an antimicrobial aqueous solution of the present invention comprises the steps of: adding and dissolving an amphipathic preservative comprising a diglycerol monolaurate at a ratio of 3.25 μg to 50 μg relative to 1 ml of water, into a water containing a sucrose monolaurate at a ratio of 0.1 μg to 100 μg relative to 1 ml of water; and adding and dissolving an ε-polylysine at a ratio of 8 μg to 30 μg relative to 1 ml of water, into the obtained aqueous solution of the amphipathic preservative; thereby exhibiting such an excellent effect to allow for obtainment of an antimicrobial aqueous solution having such an improved antimicrobial effect which is active even against gram negative bacteria by virtue of the synergistic action of the diglycerol monolaurate and ε-polylysine.

In the preparation method of an antimicrobial aqueous solution, when the diglycerol monolaurate is dissolved into the water containing the sucrose monolaurate, the dissolution is conducted at a temperature in a range from an ordinary temperature to a room temperature; thereby exhibiting such an excellent effect not only to allow for establishment of a complete aqueous solution of the diglycerol monolaurate without heating, but also to avoid deterioration of the antimicrobial effect.

DETAILED DESCRIPTION OF THE PREFERRED EMBODIMENTS

The present invention will be described more specifically, with reference to Examples. However, the technical scope of the present invention is not limited thereto.

EXAMPLE 1

[Preparation of Aqueous Solution Containing Monolaurin and ε-Polylysine Formulations, and its Antimicrobial Activity]

100 mg of a sucrose monolaurate (Ryoto Sugar Ester L1695 produced by Mitsubishi-Kagaku Foods Corporation) was dissolved in 1 liter of a sterilized deionized water, the resultant solution was heated to 50° C., 50 mg of monolaurin (Taiyo Kagaku Co., Ltd.) was added thereinto followed by stirring, the dissolution thereof was then confirmed, and the resultant solution was subsequently cooled down to a room temperature. Added into the solution was 50 mg of an ε-polylysine product (50% dextrin powder produced by Chisso Corporation; containing 50% of ε-polylysine bromate and 50% of dextrin), followed by dissolution thereof, to obtain an antimicrobial aqueous solution. This antimicrobial aqueous solution contained 25 μg/ml of the ε-polylysine, 50 μg/ml of the monolaurin, and 100 μg/ml of the sucrose monolaurate. Here, used as the monolaurin was that recrystallized by means of hexane, because a monolaurin of high purity was required. The antimicrobial aqueous solution was examined by a test of antimicrobial activity against gram negative bacteria (*Pseudomonas aeruginosa*, JCM 5961) so as to ascertain a suitable ratio of monolaurin and ε-polylysine, by means of a checkerboard test where the aqueous monolaurin solution and ε-polylysine were each dissolved as a single substance in ½ TS liquid media at identical concentrations in a manner to prepare the same media containing the stepwise diluted applicable substances, respectively, and to intercrossingly mix the stepwise diluted solutions or media with each other on microwells, respectively. Subsequently conducted was a test for the thus combined antibacterial agents, in a manner to use inoculums which were each prepared by: firstly inoculating *Pseudomonas* by an anse onto 50 ml of liquid TS medium of ½ concentration; culturing the medium at 37° C. for 18 hours to obtain an inoculum; and adjusting the same medium to a turbidity ($10^8$ CFU) of the MacFaland standard solution No. 1, to adopt the medium as a final inoculum.

Figure 1:
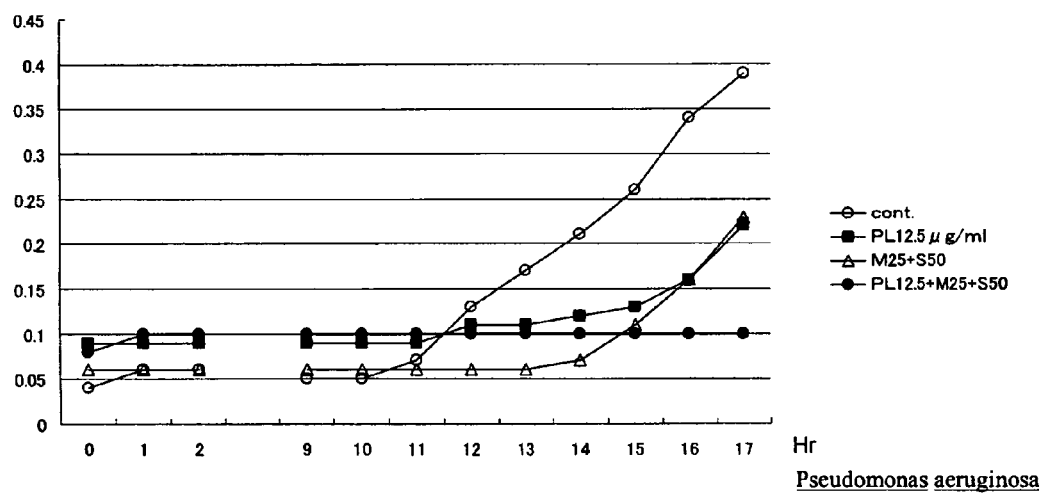
FIG. 1 is a graph showing a synergistic antimicrobial action of an antimicrobial aqueous solution utilizing a monolaurin according to the present invention.

To measure the activity of an antimicrobial aqueous solution (containing 25 μg/ml of monolaurin, 12.5 μg/ml of ε-polylysine, and 50 μg/ml of sucrose monolaurate) obtained by 2-fold diluting the above prepared antimicrobial aqueous solution, the growth curve of *Pseudomonas* was plotted by an optical density measuring method adopting a liquid culture (½ TS medium) of *Pseudomonas*. The obtained result is shown in FIG. 1. In FIG. 1, the sample (M25+S50) including only 25 μg/ml of monolaurin underwent a rapid growth of bacteria after a lapse of 14 hours. The sample (PL12.5) including only 12.5 μg/ml of ε-polylysine underwent a gradual growth of bacteria after a lapse of 12 hours. Nonetheless, the sample (PL12.5+M25+S50) including 12.5 μg/ml of ε-polylysine combined with 25 μg/ml of monolaurin exhibited a remarkable growth obstruction against bacteria.

Further, the above-described antimicrobial aqueous solution (50 μg/ml of monolaurin, and 25 μg/ml of ε-polylysine) was stepwise diluted on ½ TS media to prepare diluted solutions; one droplet of an inoculum of *Staphylococcus aureus* (FDA 209P) as gram positive bacteria or *Candida albicans* (TIMM3314) as true fungi was dropped onto 5 ml of each stepwise diluted solution by a Pasteur pipette; the resultant sample solutions were subjected to a shaking treatment at 37° C. for 2 hours; and 0.2 ml of each sample solution was dropped onto an agar plate and spread over the whole surface thereof, followed by cultivation at 37° C. for 18 hours, to subsequently observe an expression of colonies. As a result, colonies were never found from a formulated solution to a 20-fold diluted solution, thereby meaning a complete prevention. The concentrations of the respective components of the 20-fold diluted solution were 2.5 μg/ml for monolaurin and 1.25 μg/ml for ε-polylysine. In this way, it was revealed that even the 20-fold diluted concentration had exhibited a growth obstructing effect against fungi and bacteria, insofar as against gram positive bacteria, true fungi, and the like other than gram negative bacteria.

Note that dilution of an ε-polylysine by itself down to about 6.25 μg/ml was confirmed to promote growth of bacteria and fungi. This provided a suggestion that the ε-polylysine has such a bifacial action to exhibit a growth obstruction effect against bacteria and fungi at high concentrations and a growth promotion effect at low concentrations within a range of microgram unit amounts, and that a turning concentration is present near such a diluted concentration.

EXAMPLE 2

[Preparation of Aqueous Solution Containing Monolaurin and 6-Polylysine Formulations, and its Antimicrobial Activity]

100 mg of a sucrose monolaurate was dissolved in 1 liter of a sterilized deionized water; 40 mg of monolaurin (Taiyo Kagaku Co., Ltd.) was subsequently added into the resultant solution followed by stirring, the dissolution thereof was then confirmed; 50 mg of an ε-polylysine product (50% dextrin powder produced by Chisso Corporation) was added into the solution, followed by stirring for dissolution, to obtain an antimicrobial aqueous solution. This antimicrobial aqueous solution contained 25 μg/ml of the ε-polylysine, 40 μg/ml of the monolaurin, and 100 μg/ml of the sucrose monolaurate. The antimicrobial aqueous solution was subjected to a qualitative test adopting agar plates using ½ liquid media similarly to Example 1, and no colonies were expressed on the respective plates.

EXAMPLE 3

[Preparation of Aqueous Solution Combiningly Containing Diglycerol Monolaurate (Hereinafter Abbreviated to "Dilaurin") and ε-Polylysine Formulations, and its Antimicrobial Activity]

50 mg of a sucrose monolaurate (Ryoto Sugar Ester L1695 produced by Mitsubishi-Kagaku Foods Corporation) was dissolved in 1 liter of a sterilized deionized water; 50 mg of a dilaurin (product name: Q-12D produced by Taiyo Kagaku Co., Ltd.) was dissolved in the resultant solution at a room temperature of 18° C.; and then 100 mg of an ε-polylysine product (50% dextrin powder produced by Chisso Corporation; corresponding to 50 mg of ε-polylysine) was added into the solution, to prepare an antimicrobial aqueous solution. This antimicrobial aqueous solution contained 50 µg/ml of the ε-polylysine, 50 µg/ml of the dilaurin, and 50 µg/ml of the sucrose monolaurate.

The obtained antimicrobial aqueous solution was 5-fold diluted to prepare an antimicrobial aqueous solution containing 10 µg/ml of the dilaurin, 10 µg/ml of the ε-polylysine, and 10 µg/ml of the sucrose monolaurate; and a growth curve thereof was plotted so as to measure its antimicrobial activity, by the optical density measuring method using the liquid culture (½ TS medium) of *Pseudomonas*. The obtained result is shown in FIG. 2.

Figure 2:
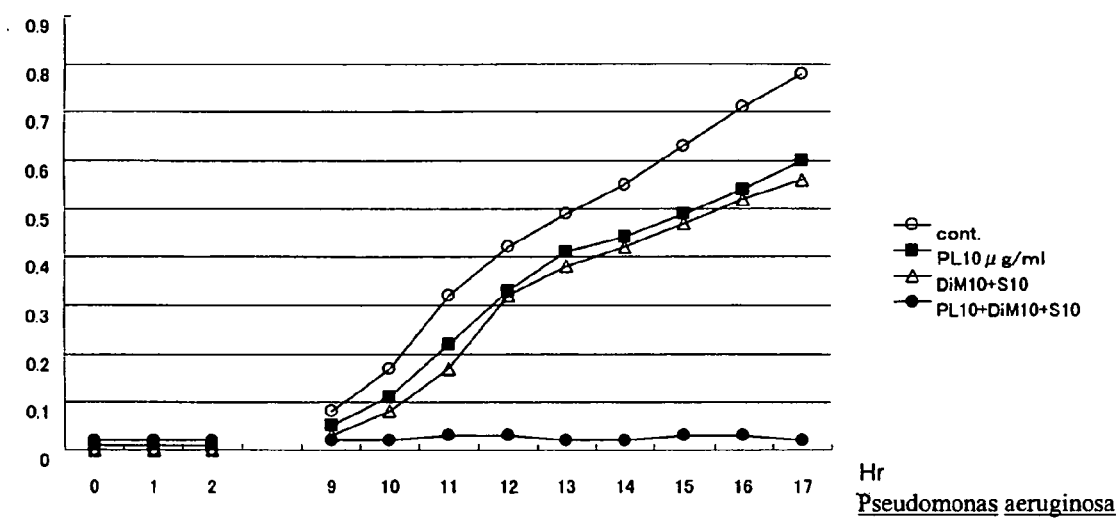
FIG. 2 is a graph showing a synergistic antimicrobial action of an antimicrobial aqueous solution utilizing a dilaurin according to the present invention.

As shown in FIG. 2, although the solutions containing 10 µg/ml of dilaurin only (DiM10+S10) and 10 µg/ml of ε-polylysine only (PL10), respectively, exhibited growth of bacteria to the similar level as a control (cont) without additive, the mixed solution (PL10+DiM10+S10) of ε-polylysine+dilaurin exhibited a remarkable effect to restrict bacteria growth.

Further, successive 2-fold dilutions were conducted for an antimicrobial aqueous solution containing 8 µg/ml of ε-polylysine and 50 µg/ml of dilaurin by utilizing sterilized TS media of ½ concentration; 5 ml of the applicable diluted solution at each fold was separately poured into dual test tubes, for preparation; while simultaneously preparing diluted solutions of ε-polylysine only in test tubes as a comparative test, in the same manner as the above; and one droplet of an inoculum of *Pseudomonas* was inoculated into each diluted solution, followed by shaking and culturing at 37° C. for 18 hours. Judgment of each activity was conducted by visually observing a growth of bacteria, and the observation result is shown by marks of + and −. The thus obtained result is shown in Table 1.

TABLE 1

| Dilution rate | µg/ml | 0 | ×2 | ×4 | ×8 | ×16* |
|---|---|---|---|---|---|---|
| ε-polylysine | 50 | − | − | − | +++ | +++ |
| ε-polylysine + diglycerol monolaurate | 8 (fix) 50 | − | − | − | − | − |

*×16 = ε-polylysine 8 µg/ml + diglycerol monolaurate 3.25 µg/ml

As shown in Table 1, although the concentration of ε-polylysine was kept constant at 8 µg/ml even by the successive 2-fold dilution, the concentration of dilaurin was stepwise diluted by dilution of 0-fold to 16-fold in a manner of 50 µg/ml, 25 µg/ml, 12.5 µg/ml, 6.25 µg/ml, and 3.25 µg/ml. In case of the ε-polylysine only, growth of bacteria was found in the dilutions of 8-fold and more. Meanwhile, the mixed liquids of ε-polylysine+dilaurin exhibited growth obstruction effects against bacteria, even when diluted down to 3.25 µg/ml.

In case of the antimicrobial aqueous solution of the present invention, the ε-polylysine is added therein within a range of microgram unit amounts, in a manner to synergetically reinforce: the strong cell surface modifying action against gram negative bacteria to be exhibited by the ε-polylysine at a lower concentration; and the antimicrobial action of the monolaurin. Further, both the ε-polylysine and monolaurin are biodegradable and are thus free of biological accumulation, and the antimicrobial aqueous solution can be provided in a completely dissolved form. Moreover, since the antimicrobial aqueous solution can be provided in a colorless, odorless, and tasteless form, the antimicrobial aqueous solution has an extremely wide range of applications as an antibacterial agent of a broad spectrum from a social standpoint, such as: (1) usage in a large amount, as an air spray or cleaning water for exterminating harmful micro-organisms on a social scale; (2) usage as an antiseptic solution for sanitary supervision at a medical front or an advanced person facility; (3) usage as an antibacterial agent in a daily life; and (4) usage as an antibacterial agent as a countermeasure for mitigating a body order or the like.

What is claimed is:

1. An antimicrobial aqueous solution comprising:
an aqueous solution containing:
25 µg/ml to 50 µg/ml of an amphipathic preservative comprising a monoglycerol monolaurate;
12.5 µg/ml to 30 µg/ml of an ε-polylysine; and
0.1 µg/ml to 100 µg/ml of a sucrose monolaurate.

2. An antimicrobial aqueous solution comprising:
an aqueous solution containing:
3.25 µg/ml to 50 µg/ml of an amphipathic preservative comprising a diglycerol monolaurate;
8 µg/ml to 30 µg/ml of an ε-polylysine; and
0.1 µg/ml to 100 µg/ml of a sucrose monolaurate.

3. A method for reducing or eliminating bacteria, said method comprising treating said bacteria with said antimicrobial aqueous solution of claim 1.

4. The method according to claim 3, wherein said bacteria is gram negative.

5. The method according to claim 4, wherein said bacteria is *Pseudomonas* bacteria.

6. The method according to claim 3, wherein said bacteria is gram positive.

7. The method according to claim 6, wherein said bacteria is *Staphylococcus aureus* or *Candida albicans*.

8. The method according to claim 3, wherein said antimicrobial aqueous solution is diluted with deionized water.

9. The method according to claim 8, wherein the dilution is 2 to 16-fold with said water.

10. The method according to claim 8, wherein the pH of said antimicrobial aqueous solution is 4 to 8.

11. The antimicrobial aqueous solution according to claim 1, comprising 0.1 µg/ml to 50 µg/ml of said sucrose monolaurate.

12. The antimicrobial aqueous solution according to claim 2, comprising 0.1 µg/ml to 30 µg/ml of said sucrose monolaurate.

13. The antimicrobial aqueous solution according to claim 1, further comprising an aqueous ethanol solution of 30-60%.

14. The antimicrobial aqueous solution according to claim 2, further comprising an aqueous ethanol solution of 30-60%.

15. An antimicrobial aqueous solution consisting essentially of:
25 µg/ml to 50 µg/ml of an amphipathic preservative comprising a monoglycerol monolaurate;
12.5 µg/ml to 30 µg/ml of an ε-polylysine; and
0.1 µg/ml to 100 µg/ml of a sucrose monolaurate.

16. An antimicrobial aqueous solution consisting essentially of:
3.25 µg/ml to 50 µg/ml of an amphipathic preservative comprising a diglycerol monolaurate;
8 µg/ml to 30 µg/ml of an ε-polylysine; and
0.1 µg/ml to 100 µg/ml of a sucrose monolaurate.

17. An antimicrobial aqueous solution consisting essentially of:

25 µg/ml to 50 µg/ml of an amphipathic preservative comprising a monoglycerol monolaurate;
12.5 µg/ml to 30 µg/ml of an ε-polylysine;
0.1 µg/ml to 100 µg/ml of a sucrose monolaurate; and
an aqueous ethanol solution of 30-60%.

18. An antimicrobial aqueous solution consisting essentially of:

3.25 µg/ml to 50 µg/ml of an amphipathic preservative comprising a diglycerol monolaurate;
8 µg/ml to 30 µg/ml of an ε-polylysine;
0.1 µg/ml to 100 µg/ml of a sucrose monolaurate; and
an aqueous ethanol solution of 30-60%.

* * * * *

UNITED STATES PATENT AND TRADEMARK OFFICE
CERTIFICATE OF CORRECTION

PATENT NO. : 8,377,870 B2
APPLICATION NO. : 12/738021
DATED : February 19, 2013
INVENTOR(S) : Setsuo Takeuchi et al.

It is certified that error appears in the above-identified patent and that said Letters Patent is hereby corrected as shown below:

At column 10 line 45, "6-Polylysine" should read: --ε-Polylysine--

Signed and Sealed this
Second Day of April, 2013

Teresa Stanek Rea
*Acting Director of the United States Patent and Trademark Office*